(12) United States Patent
Zhang et al.

(10) Patent No.: US 8,221,323 B2
(45) Date of Patent: Jul. 17, 2012

(54) USING ACOUSTIC ENERGY TO COMPUTE A LUNG EDEMA FLUID STATUS INDICATION

(75) Inventors: Yunlong Zhang, Mounds View, MN (US); Yongxing Zhang, Maple Grove, MN (US); Paul E. Zarembo, Vadnais Heights, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 901 days.

(21) Appl. No.: 11/833,502

(22) Filed: Aug. 3, 2007

(65) Prior Publication Data

US 2009/0036777 A1 Feb. 5, 2009

(51) Int. Cl.
*A61B 8/00* (2006.01)
(52) U.S. Cl. .................................. 600/437; 600/459
(58) Field of Classification Search .................. 600/407, 600/437, 459, 462
See application file for complete search history.

(56) References Cited

U.S. PATENT DOCUMENTS

| | | | | |
|---|---|---|---|---|
| 4,880,009 A | * | 11/1989 | Yanagawa | 600/445 |
| 5,213,098 A | | 5/1993 | Bennett et al. | |
| 6,076,015 A | | 6/2000 | Hartley et al. | |
| 6,104,949 A | | 8/2000 | Pitts et al. | |
| 6,186,962 B1 | | 2/2001 | Lloyd et al. | |
| 6,358,208 B1 | * | 3/2002 | Lang et al. | 600/438 |
| 6,527,729 B1 | | 3/2003 | Turcott | |
| 6,665,564 B2 | | 12/2003 | Lincoln et al. | |
| 6,795,732 B2 | | 9/2004 | Stadler et al. | |
| 6,931,272 B2 | | 8/2005 | Burnes | |
| 6,959,214 B2 | | 10/2005 | Pape et al. | |
| 6,963,777 B2 | | 11/2005 | Lincoln et al. | |
| 7,024,248 B2 | | 4/2006 | Penner et al. | |
| 7,082,330 B2 | | 7/2006 | Stadler et al. | |
| 7,096,064 B2 | | 8/2006 | Deno et al. | |
| 7,177,681 B2 | | 2/2007 | Zhu et al. | |

(Continued)

FOREIGN PATENT DOCUMENTS

EP 1151719 A2 11/2001
(Continued)

OTHER PUBLICATIONS

"Pulmonary edema", http://en.wikipedia.org/wiki/Pulmonary_edema, (Archived Apr. 6, 2004), 3 Pages.

(Continued)

*Primary Examiner* — Tse Chen
*Assistant Examiner* — Peter Luong
(74) *Attorney, Agent, or Firm* — Schwegman, Lundberg & Woessner, P.A.

(57) ABSTRACT

Systems and methods for monitoring lung edema fluid status, such as monitoring the presence or absence of pulmonary edema, in a subject using information about responsive acoustic energy echoes from a lung are described. The system comprises, among other things, an implantable device including an acoustic transducer configured to emit acoustic energy to a lung and to receive one or more responsive acoustic energy echoes from a lung. In an example, the implantable device includes a cardiac function management device having an acoustic window in a body thereof. In another example, the implantable device includes one or more subcutaneous leads. An implantable or external processor circuit is configured to receive information about the acoustic energy echoes to compute and provide a lung edema fluid status indication; such information may include an increased number or special pattern of acoustic energy echoes received or a decreased time between successively received echoes.

25 Claims, 11 Drawing Sheets

U.S. PATENT DOCUMENTS

| | | | |
|---|---|---|---|
| 7,186,220 | B2 | 3/2007 | Stahmann et al. |
| 7,272,443 | B2 | 9/2007 | Min et al. |
| 7,340,296 | B2 | 3/2008 | Stahmann et al. |
| 7,387,610 | B2 | 6/2008 | Stahmann et al. |
| 7,437,192 | B2 | 10/2008 | Gill et al. |
| 7,480,528 | B2 | 1/2009 | Brockway et al. |
| 7,574,255 | B1* | 8/2009 | Min .............................. 600/547 |
| 7,628,757 | B1 | 12/2009 | Koh |
| 7,672,718 | B2 | 3/2010 | Stahmann et al. |
| 2004/0127790 | A1 | 7/2004 | Lang et al. |
| 2005/0143777 | A1 | 6/2005 | Sra |
| 2005/0182330 | A1 | 8/2005 | Brockway et al. |
| 2006/0100666 | A1 | 5/2006 | Wilkinson et al. |
| 2006/0258952 | A1 | 11/2006 | Stahmann et al. |
| 2006/0293609 | A1 | 12/2006 | Stahmann et al. |
| 2007/0055184 | A1 | 3/2007 | Echt et al. |
| 2007/0088214 | A1* | 4/2007 | Shuros et al. ................. 600/437 |
| 2007/0088221 | A1 | 4/2007 | Stahmann |
| 2007/0167758 | A1* | 7/2007 | Costello ........................ 600/437 |
| 2008/0058885 | A1 | 3/2008 | Belalcazar et al. |
| 2008/0108907 | A1 | 5/2008 | Stahmann et al. |
| 2008/0249433 | A1 | 10/2008 | Stahmann et al. |
| 2009/0012416 | A1 | 1/2009 | Belalcazar et al. |
| 2009/0035596 | A1 | 2/2009 | Higashi |
| 2009/0069708 | A1 | 3/2009 | Hatlestad et al. |
| 2009/0132000 | A1 | 5/2009 | Brockway et al. |
| 2010/0022911 | A1 | 1/2010 | Wariar et al. |
| 2010/0076336 | A1 | 3/2010 | Stahmann |
| 2011/0009746 | A1 | 1/2011 | Tran et al. |

FOREIGN PATENT DOCUMENTS

| | | | |
|---|---|---|---|
| EP | 1238630 | A2 | 9/2002 |
| JP | 4-82538 | A | 3/1992 |
| JP | 6-287132 | A | 10/1994 |
| JP | 2003-530940 | A | 10/2003 |
| JP | 2007-508861 | A | 4/2007 |
| WO | WO-2006/028575 | A2 | 3/2006 |
| WO | WO-2006/127719 | A2 | 11/2006 |
| WO | WO-2007/002992 | A1 | 1/2007 |
| WO | WO-2009/005559 | A1 | 1/2009 |
| WO | WO-2009/020571 | A1 | 2/2009 |
| WO | WO-2011005953 | A2 | 1/2011 |
| WO | WO-2011005953 | A3 | 3/2011 |

OTHER PUBLICATIONS

Jambrik, Z., et al., "Usefulness of ultrasound lung comets as a nonradiologic sign of extravascular lung water", *Am J Cardiol.*, 93(10), (May 15, 2004), 1265-1270.

Lichtenstein, D., et al., "A lung ultrasound sign allowing bedside distinction between pulmonary edema and COPD: the comet-tail artifact.", *Intensive Care Med.*, 24(12), (Dec. 1998), 1331-4.

"International Application Serial No. PCT/US2008/009342, International Search Report mailed Nov. 5, 2008", 4 pgs.

"International Application Serial No. PCT/US2008/009342, Written Opinion mailed Nov. 5, 2008", 6 pgs.

Adamson, P. B, et al., "Ongoing right ventricular hemodynamics in heart failure: clinical value of measurements derived from an implantable monitoring system.", *J Am Coll Cardiol.*, 41(4), (Feb. 19, 2003), 565-571.

Hunt, S. A, et al., "ACC/AHA 2005 guideline update for the diagnosis and management of chronic heart failure in the adult: a report of the American College of Cardiology/American Heart Association Task Force on Practice Guidelines", *J Am Coll Cardiol.*, 46(6), (Writing Committee to Update the 2001 Guidelines for the Evaluation and Management of Heart Failure)., (Sep. 20, 2005), e1-e82.

Pasterkamp, H., et al., "Respiratory sounds. Advances beyond the stethoscope", *Am J. Respir Crit Care Med.*, 156(3 Pt 1), (Sep. 1997), 974-987.

Rasanen, J., et al., "Detection of porcine oleic acid-induced acute lung injury using pulmonary acoustics.", *J Appl Physiol.*, 93(1), (Jul. 2002), 51-57.

Wagoner, L. E, et al., "Cardiac Function and Heart Failure", *J Am Coll Cardiol.*, 47(11)(Suppl D), (Jun. 6, 2006), D18-D22.

"International Application U.S. Appl. No. PCT/US2010/041360, Invitation to Pay Additional Fee mailed Nov. 2, 2010", 6 pgs.

"International Application U.S. Appl. No. PCT/US2010/041360, Search Report mailed Jan. 18, 2011", 6 pgs.

"International Application U.S. Appl. No. PCT/US2010/041360, Written Opinion mailed Jan. 18, 2011", 8 pgs.

"International Application Serial No. PCT/US2010/041360, International Preliminary Report on Patentability issued Jan. 10, 2012", 9 pgs.

"Japanese Application Serial No. 2010-519948, Office Action mailed May 22, 2012", (w/ English Translation), 5 pgs.

\* cited by examiner

USING ACOUSTIC ENERGY TO COMPUTE A LUNG EDEMA FLUID STATUS INDICATION

TECHNICAL FIELD

This patent document pertains generally to medical systems and methods. More particularly, but not by way of limitation, this patent document pertains to fluid monitoring systems and methods configured for using information about one or more responsive ultrasound or other acoustic energy echoes from a lung to compute a lung edema fluid status indication.

BACKGROUND

Excess fluid retention in a subject can take various forms and can have different causes. Clinically, this fluid retention is called edema and can be classified as systemic or pulmonary edema. Examples of systemic edema include excess fluid accumulation in a subject's lower limbs, sacral area, abdominal cavity, or other parts of the body that receive blood through the aorta. Pulmonary edema involves a build-up of extravascular fluid in or around a subject's lungs.

One cause of pulmonary edema is congestive heart failure ("CHF"), sometimes referred to simply as "heart failure." Heart failure is a major health problem—it is estimated that 5 million people suffer heart failure in the United States alone and it is believed to be growing at an approximate rate of 550,000 new cases each year due to, among other things, overall demographic aging. CHF can be conceptualized as an enlarged weakened heart muscle. As CHF worsens, the impaired heart muscle results in poor cardiac output of blood. Consequently, pulmonary circulatory pressure increases resulting in fluid leakage into extravascular spaces, pooling therein. This fluid pooling affects compliance of lung and oxygen exchange. For this reason, pulmonary edema can be an indicator of worsening or decompensated CHF.

Pulmonary edema can present a medical emergency that requires immediate care. The outlook for pulmonary edema patients can be good if detected early and treated promptly. If left undetected, and consequently untreated, pulmonary edema can lead to extensive hospitalization and even death.

Overview

The present inventors have recognized, among other things, that one problem presented by heart failure is its timely detection and treatment. The present inventors have further recognized that there exists an unmet need for enhanced sensitivity or specificity monitoring of excess fluid accumulation in the thoracic region of a subject, such as the subject's lungs, before the need for hospitalization or progression to advanced disease stage arise.

Systems and methods for monitoring lung edema fluid status, such as monitoring the presence or absence of pulmonary edema, in a subject using information about responsive acoustic energy echoes from a lung are described. The system comprises, among other things, an implantable device including an acoustic transducer configured to emit acoustic energy to a lung and to receive one or more responsive acoustic energy echoes from a lung. In an example, the implantable device includes a cardiac function management device having an acoustic window in a body thereof. In another example, the implantable device includes one or more subcutaneous leads. An implantable or external processor circuit is configured to receive information about the acoustic energy echoes to compute and provide a lung edema fluid status indication; such information may include an increased number or special pattern of acoustic energy echoes received or a decreased time between successively received echoes.

In Example 1, a system comprises a fully implantable device including an acoustic transducer configured to emit acoustic energy to a lung and to receive a responsive acoustic energy echo from a lung; and an implantable or external processor circuit configured to receive information about the acoustic energy echo and to use the information about the acoustic energy echo to compute and provide a lung edema fluid status indication.

In Example 2, the system of Example 1 is optionally configured such that the information about the acoustic energy echo includes a number of acoustic energy echoes per unit of time.

In Example 3, the system of at least one of Examples 1-2 optionally comprises an external user-interface device communicatively coupled to the implantable device and including a user-detectable indication of lung edema fluid status derived from the information about the acoustic energy echo.

In Example 4, the system of Example 3 is optionally configured such that the external user-interface device includes a user input device configured for receiving a programmable acoustic energy echo measurement parameter from a user and communicating the measurement parameter to the implantable device.

In Example 5, the system of at least one of Examples 1-4 optionally comprises a transducer pulse control circuit configured to control at least one of an amplitude, a frequency, or a duration of the acoustic energy emitted from the acoustic transducer and thereby provide a level of confidence in the computed lung edema fluid status indication.

In Example 6, the system of at least one of Examples 1-5 optionally comprises a plurality of acoustic transducers configured to be distributed near or directly adjacent one or both lungs.

In Example 7, the system of at least one of Examples 1-6 optionally comprises a comparator circuit configured to compare an energy of the acoustic energy echo to a stored specified threshold, algorithm, pattern, or data array; and is optionally configured such that the processor circuit uses information about the comparison to compute the lung edema fluid status indication.

In Example 8, the system of at least one of Examples 1-7 optionally comprises a timing circuit configured to trigger a recurrent emitting of the acoustic energy synchronized with a specified phase of one or both of a subject's respiratory cycle or cardiac cycle.

In Example 9, the system of at least one of Examples 1-8 optionally comprises a memory circuit configured to store information about different instances of the acoustic energy echo over a period of time that exceeds a respiration cycle length time.

In Example 10, the system of at least one of Examples 1-9 optionally comprises a regimen control circuit configured to initiate or adjust a regimen provided to a subject using information about the acoustic energy echo.

In Example 11, the system of at least one of Examples 1-10 optionally comprises a pressure sensor configured to provide a blood pressure-indicating signal indicative of blood pressure in a pulmonary artery; and is optionally configured such that the processor circuit includes an input to receive the blood pressure-indicating signal and use such information to compute the lung edema fluid status indication.

In Example 12, the system of at least one of Examples 1-11 optionally comprises an electrical impedance measurement circuit configured to inject an electrical energy between two or more electrodes and to concurrently measure a response thereto in a thoracic region of a subject between the same or different two or more electrodes to provide a thoracic impedance-indicating signal; and is optionally configured such that the processor circuit includes an input to receive the thoracic impedance-indicating signal and use such information to compute the lung edema fluid status indication.

In Example 13, the system of at least one of Examples 1-12 is optionally configured such that the implantable device includes a cardiac function management device having a device body.

In Example 14, the system of Example 13 is optionally configured such that the device body includes an acoustic window, the acoustic window disposed such that the acoustic energy is emitted or responsive acoustic energy is received therethrough in a direction of a lung when the device body is implanted in a pectoral region.

In Example 15, the system of at least one of Examples 1-14 is optionally configured such that the implantable device includes one or more subcutaneous leads, each lead having a lead body extending from a proximal end portion to a distal end portion and having an intermediate portion therebetween; and such that at least one of the intermediate portion or the distal end portion includes the acoustic transducer.

In Example 16, the system of at least one of Examples 1-15 is optionally configured such that the acoustic energy includes a frequency within an inclusive range of about 20 KHz to about 10 MHz.

In Example 17, a method comprises emitting acoustic energy toward a lung using a fully implantable device; receiving and processing an acoustic energy echo; and computing and providing a lung edema fluid status indication using information about the acoustic energy echo.

In Example 18, the method of Example 17 is optionally configured such that computing and providing the lung edema fluid status indication includes recognizing at least one of an increase in the number of acoustic energy echoes received or a decrease in time between successively received acoustic energy echoes.

In Example 19, the method of at least one of Examples 17-18 optionally comprises providing a user-detectable indication of lung edema fluid status, including displaying information about the acoustic energy echo.

In Example 20, the method of Example 19 is optionally configured such that providing the user-detectable indication includes displaying the presence or absence of one or more comet-tail-like artifacts.

In Example 21, the method of at least one of Examples 17-20 optionally comprises automatically determining the presence or absence of one or more comet-tail-like artifacts using a programmably learned or defined algorithm.

In Example 22, the method of at least one of Examples 17-21 optionally comprises programmably or automatically changing at least one of an amplitude, a frequency, pulse shape, or a duration of the acoustic energy.

In Example 23, the method of at least one of Examples 17-22 optionally comprises programmably or automatically selecting which one or more acoustic transducers are used to emit the acoustic energy.

In Example 24, the method of at least one of Examples 17-23 optionally comprises storing information about instances of the acoustic energy echo over a period of time that exceeds a respiration cycle length.

In Example 25, the method of at least one of Examples 17-24 optionally comprises measuring an indication of pulmonary artery blood pressure; and also using the indication of pulmonary artery blood pressure to compute the lung edema fluid status indication.

In Example 26, the method of at least one of Examples 17-25 optionally comprises measuring an indication of thoracic impedance; and also using the indication of thoracic impedance to compute the lung edema fluid status indication.

In Example 27, the method of at least one of Examples 17-26 optionally comprises measuring an indication of at least one heart sound; and also using the indication of heart sound to compute the lung edema fluid status indication.

In Example 28, the method of at least one of Examples 17-27 optionally comprises measuring at least one of a blood flow indication, a heart size indication, a venous pressure indication, a respiration rate indication, or an associated rate of change thereof; and also using at least one of the blood flow indication, the heart size indication, the venous pressure indication, the respiration rate indication, or the associate rate of change thereof to compute the lung edema fluid status indication.

In Example 29, the method of at least one of Examples 17-28 optionally comprises adjusting an orientation of the acoustic transducer via adjusting a set-screw associated with the transducer.

In Example 30, the method of at least one of Examples 17-29 optionally comprises adjusting an orientation of the acoustic transducer via activating an implanted motor associated with the transducer.

In Example 31, the method of at least one of Examples 17-30 is optionally configured such that emitting acoustic energy includes emitting ultrasonic energy toward the lung using the fully implantable device.

In Example 32, the method of at least one of Examples 17-31 is optionally configured such that emitting acoustic energy toward the lung includes steering the acoustic energy from at least one of a left or a right pectoral region of a subject.

In Example 33, the method of at least one of Examples 17-32 is optionally configured such that emitting acoustic energy toward the lung includes steering the acoustic energy from a lateral region between a subject's ribs and left lung; and such that receiving the acoustic echo includes receiving the acoustic echo at a lateral region between the subject's ribs and right lung.

In Example 34, the method of at least one of Examples 17-33 is optionally configured such that emitting acoustic energy toward the lung includes using at least one reference marker disposed on a lead or fixated to a portion of a subject.

In Example 35, the method of at least one of Examples 17-34 is optionally configured such that computing the lung edema fluid status indication includes determining the presence or absence of pulmonary edema, including recognizing an increase in acoustic impedance from the acoustic echo.

Advantageously, the present systems and methods can provide for enhanced, yet less complex monitoring of excess fluid accumulation in a subject's thoracic region and thus, may provide a more timely, accurate, or cheaper detection of pulmonary edema or other thoracic fluid accumulation than is currently available. Such detection can be made possible by, among other things, generating one or more responsive acoustic energy echoes from a lung by emitting acoustic energy thereto, and using information about such acoustic energy echoes to compute and provide a lung edema fluid status indication. These and other examples, advantages, and features of the present fluid monitoring systems and methods will be set forth in part in the following Detailed Description. This overview is intended to provide an overview of subject matter of the present patent document. It is not intended to provide an exclusive or exhaustive explanation of the invention. The Detailed Description is included to provide further information about the present patent document.

BRIEF DESCRIPTION OF THE DRAWINGS

In the drawings, like numerals describe similar components throughout the several views. Like numerals having different letter suffixes represent different instances of similar components. The drawings illustrate generally, by way of example, but not by way of limitation, various embodiments discussed in the present document.

DETAILED DESCRIPTION

In general, an excess fluid accumulation in a region of a subject, clinically referred to simply as "edema," can be conceptualized as a failure or decompensation of one or more homeostatic processes within the subject's body. The body normally prevents the accumulation of fluids therewithin by maintaining adequate pressures and concentrations of salts and proteins, and by actively removing excess fluid. If a disease affects any of these normal bodily mechanisms or if the normal bodily mechanisms are unable to keep up with the fluid accumulation, the result can be edema, such as pulmonary edema.

Figure 1:
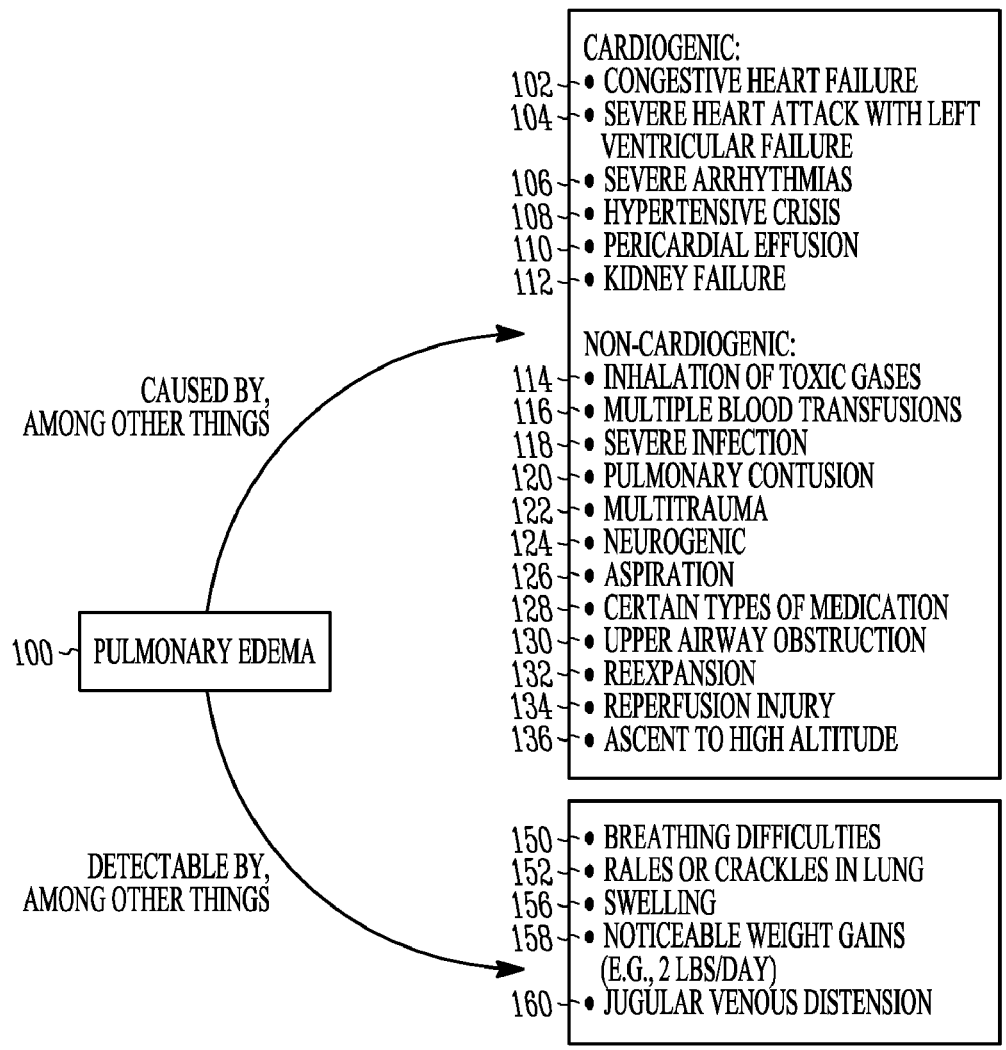
FIG. 1 is a block diagram illustrating various causes and indications of pulmonary edema in a subject.

There are several conditions or diseases that can cause or affect pulmonary edema. As shown in FIG. 1, this includes, among others, congestive heart failure 102, severe heart attack 104, severe arrhythmias 106 (either tachycardia or bradycardia), hypertensive crisis 108, pericardial effusion 110, kidney failure 112, inhalation of toxic gases 114, multiple blood transfusions 116, severe infection 118, pulmonary contusion 120, multitrauma 122 (e.g., severe car accident), neurogenic 124 (e.g., subarachnoid hemorrhage), aspiration 126 (e.g., gastric fluid), certain types of medication 128, upper airway obstruction 130, reexpansion 132, reperfusion injury 134, or ascent to high altitude 136. While pulmonary edema 100 can be a sign of many conditions or diseases, the prospect that pulmonary edema 100 can be a sign of failing heart circulation 102 is often of first concern to caregivers (e.g., health care professionals) due to the severity of its nature. Unfortunately, the first indication that an attending caregiver typically has of an occurrence of pulmonary edema 100 is very late in the disease process, such as when it becomes physically manifested by rales or crackles 152 in the subject's lung(s), swelling 156, noticeable weight gains 158, jugular venous distension 160, or breathing difficulties 150 that are so overwhelming as to be noticed by the subject, who then proceeds to be examined by his or her caregiver. For a heart failure subject, hospitalization at such a physically apparent time will likely be required.

In an effort to timely and accurately detect impending edema, such as pulmonary edema, and avoid its associated hospitalizations, the present ambulatory fluid monitoring systems and methods can compute and provide a lung edema fluid status indication using information about one or more responsive acoustic energy echoes from a lung. Such acoustic energy is not limited to audible frequencies, but can include any sound, pressure, vibration, or the like at frequencies within or outside of the range of hearing. An acoustic approach to lung edema fluid status monitoring is not readily apparent because, among other things, tissue and air acoustic impedances exhibit different characteristics, and lung passageways are designed to carry appreciable quantities of air. The present inventors have found, however, that lung monitoring and more specifically, lung fluid monitoring, is possible using information about one or more responsive acoustic energy echoes (e.g., information about the rate, pattern, or number of acoustic energy echoes). The present inventors also believe that an acoustic approach may enhance sensitivity and specificity of pulmonary edema detection.

An example of such a system comprises, among other things, a fully implantable device including at least one acoustic transducer, such as an acoustic transducer probe, configured to emit acoustic energy to a lung and to receive one or more responsive acoustic energy echoes from a lung. In an example, the implantable device includes a cardiac function management device having an acoustic window in body (e.g., a housing or header) thereof. In another example, the implantable device includes one or more transducer-bearing leads. An implantable or external processor circuit is configured to receive information about the acoustic energy echoes to compute and provide a lung edema fluid status indication. By viewing a graphical display of the acoustic energy echo information or by comparing a profile of such information to at least one of a specified threshold, algorithm, pattern or data array, a status indication of present or impending lung fluid accumulation can be computed and provided. In various examples, computation and providence of the lung edema fluid status indication includes the recognition of an increased number of acoustic energy echoes received or a decreased time between successively received acoustic energy echoes.

Figure 2:
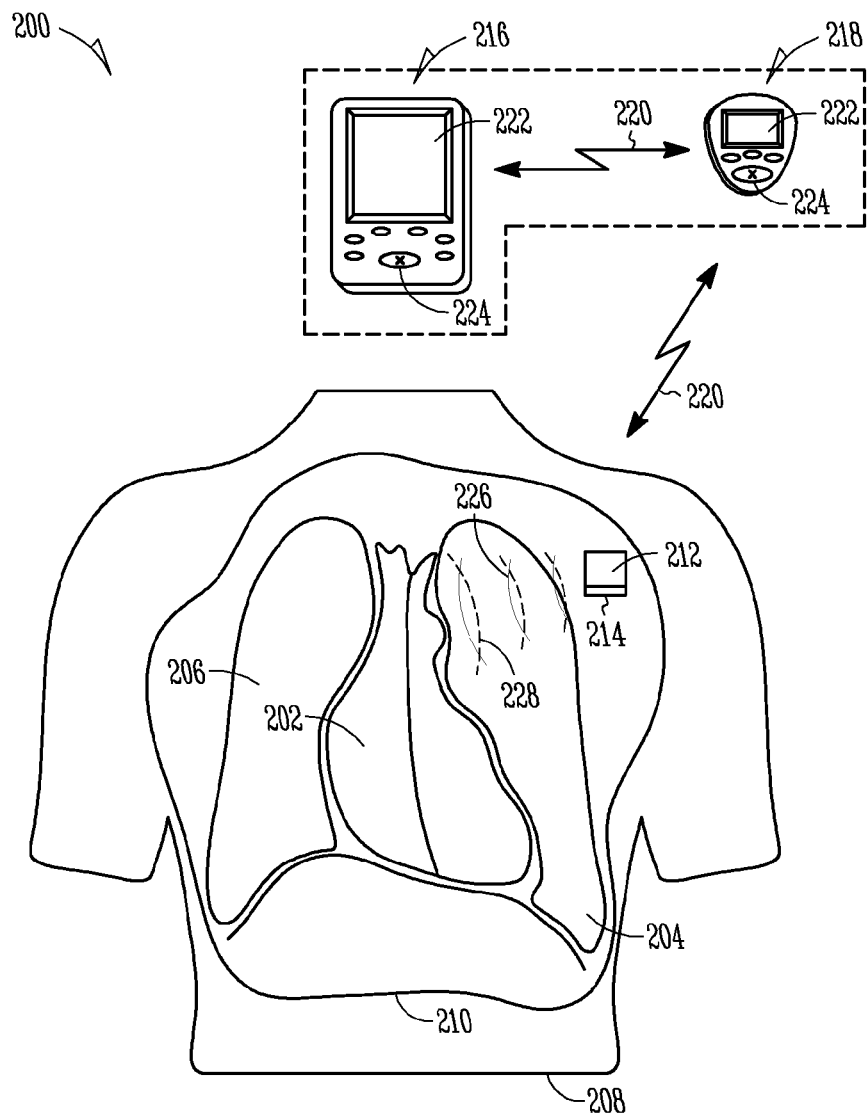
FIG. 2 is a schematic view of a system configured for monitoring excess fluid accumulation in the thoracic region of a subject by computing and providing a lung edema fluid status indication, the indication found using information about one or more responsive acoustic energy echoes from a lung.

FIG. 2 shows a heart 202 and lungs 204 (left), 206 (right) of a subject 208 (via a cut-away portion 210), and a system 200 configured for monitoring excess fluid accumulation in the lungs using information about one or more acoustic energy echoes therefrom in response to emitted acoustic energy directed thereto. In FIG. 2, the system 200 includes a pectorally-implanted device 212 including at least one acoustic transducer 214 and one or more programmers or other external user-interface devices 216, 218 providing wireless communication with the device 212, such as by using telemetry 220 or another communication technique. The at least one acoustic transducer 214, such as an acoustic transducer probe, is configured to emit ultrasound or other acoustic energy 226 to a lung 204, 206 and to receive one or more responsive ultrasound or other acoustic energy echoes 228 therefrom. An implantable 302 (see, e.g., FIG. 3A) or external 340 (see, e.g., FIG. 3B) processor circuit is configured to receive information about the acoustic energy echoes 228 and to use the echo information to compute and provide a lung edema fluid status indication, such as an indication of fluid in a lung's 204, 206 interstitial or alveolar area or extravascular fluid.

The implantable device 212 including the at least one acoustic transducer 214 can be a leaded or leadless device. For instance, it can also be built into a cardiac function management device (CFMD) 304 (see, e.g., FIG. 3A), such as a pacer, or built into one or more subcutaneous transducer-bearing leads 306 (see, e.g., FIG. 3A), such as along an intermediate or distal end portion thereof, or both. In various examples, at least one acoustic transducer 214 emits an acoustic energy beam 226 that sweeps a lung, such as the left lung 204, to determine whether or not fluid is present therein. A responsive acoustic energy echo data profile 228 is received by at least one acoustic transducer 214 and processed by a processor circuit. In various examples, an increased number of echoes received, decreased time between successive echoes received, or a special pattern of echoes received, for example, provides an indication of fluid accumulation in the lung 204.

As shown, the external user-interface devices 216, 218 can include, among other things, a user-detectable indication 222, such as an LCD or LED display, for textually or graphically relaying information about the lung edema fluid status derived from the acoustic energy echo. In various examples, a special pattern, such as one or more comet-tail-like artifacts (see, e.g., FIG. 4), is displayed if fluid accumulation is present or impending in or around the lungs 204, 206. In addition to detecting lung fluid accumulation, the display of the one or more comet-tail-like artifacts can also be used for quantification of the excessive fluid in or around the lungs. The external user-interface devices 216, 218 can further include a user input device 224 configured for receiving a programmable acoustic energy echo measurement interval from a user and communicating such interval to the implantable device 212 for implementation.

Figure 3A:
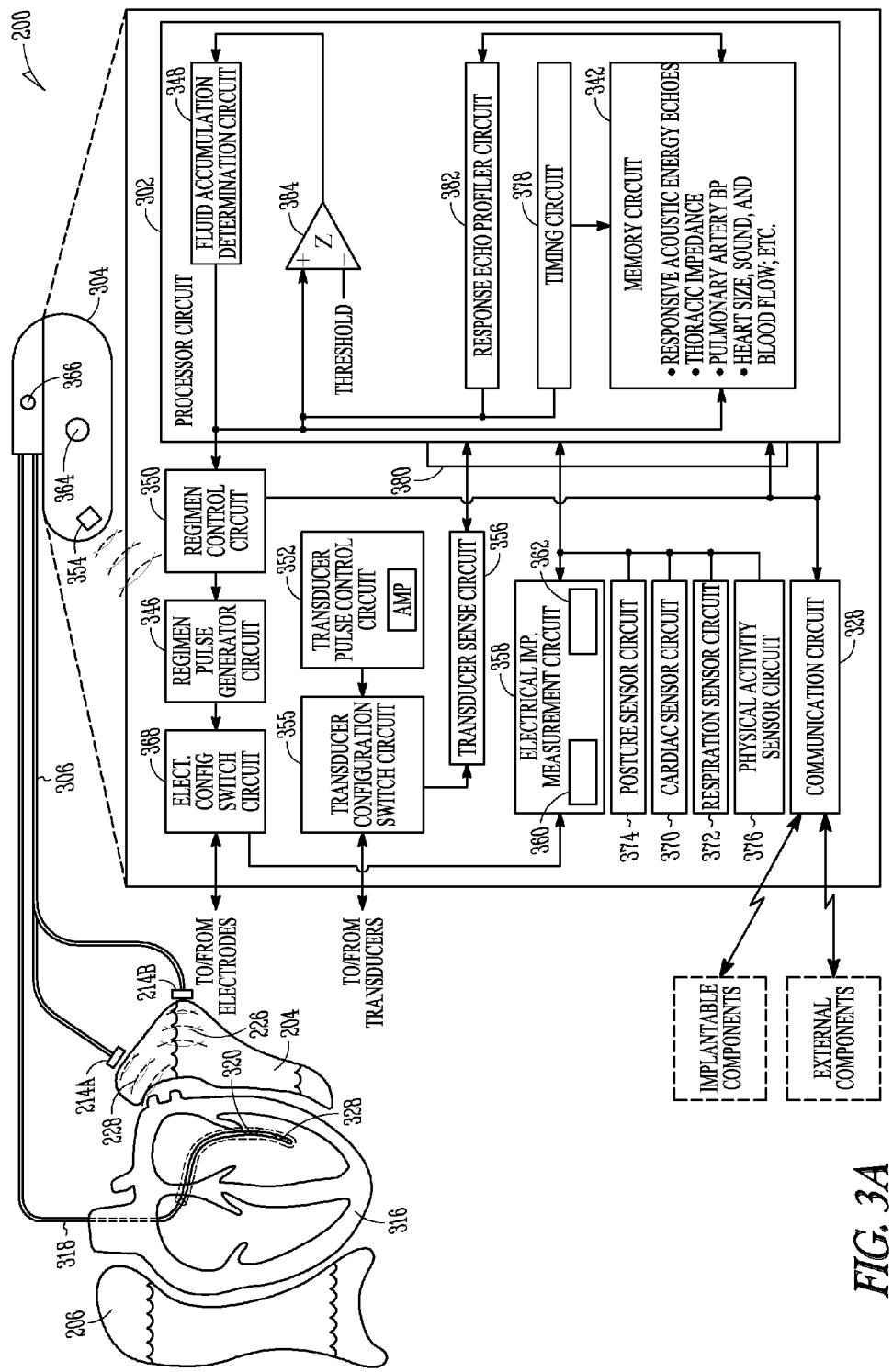
FIG. 3A is a block diagram illustrating one conceptual example of portions of a system configured for monitoring excess fluid accumulation in the thoracic region of a subject by computing and providing a lung edema fluid status indication, the indication found using information about one or more responsive acoustic energy echoes from a lung.
Figure 3B:
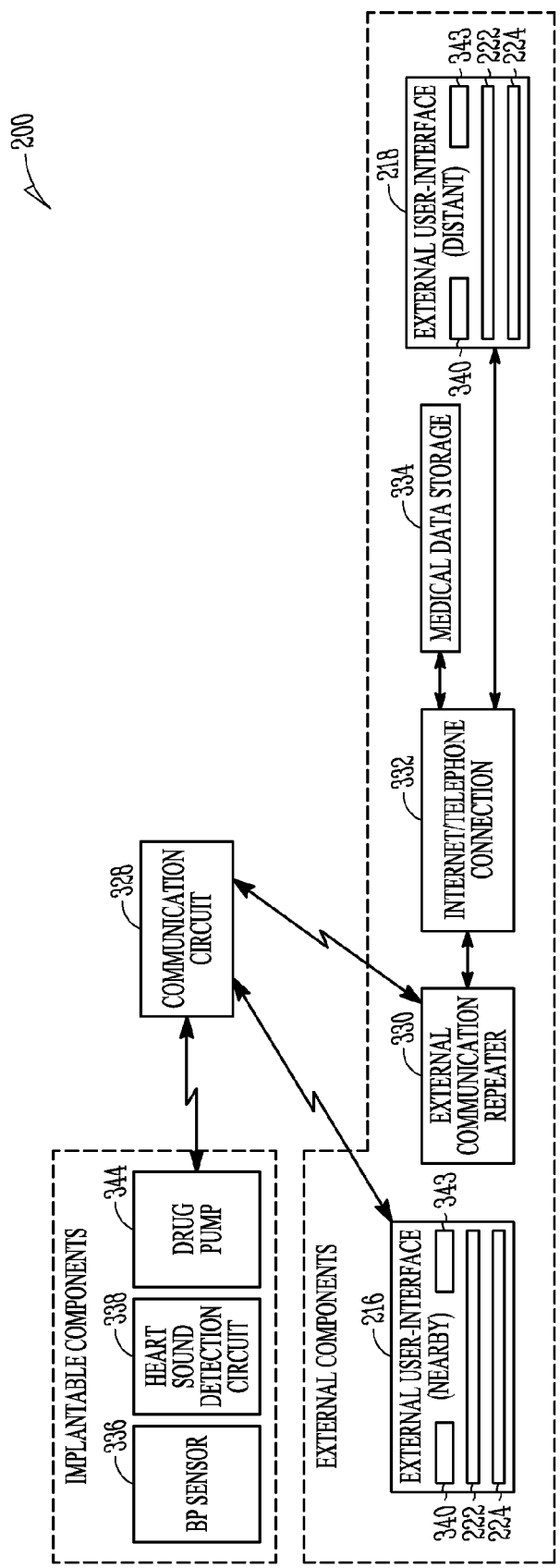
FIG. 3B is a block diagram illustrating one conceptual example of portions of a system configured for monitoring excess fluid accumulation in the thoracic region of a subject by computing and providing a lung edema fluid status indication, the indication found using information about one or more responsive acoustic energy echoes from a lung.

FIGS. 3A-3B are block diagrams illustrating generally, by way of example, but not by way of limitation, a conceptual example of a system 200 configured for monitoring excess fluid accumulation in a subject's lungs 204 (left), 206 (right), such as by using information about one or more acoustic energy echoes 228 (e.g., a number, pattern, or time between successive echoes) from a lung in response to emitted acoustic energy directed thereto. In this example, the system 200 includes a hermetically sealed CFMD 304 coupled to a subject's heart 316, such as by one or more electrode-bearing intravascular leads (e.g., a left ventricular lead 318 having electrodes 320, 322) or one or more transducer-bearing leads 306 having acoustic transducer probes 214A, 214B. The system 200 can further include one or more programmers or other external user-interface devices 216 (nearby), 218 (distant). In the example shown, the CFMD 304 includes circuitry for measuring responsive acoustic energy echoes, such as at specified times (e.g., when the subject 208 (FIG. 2) is at rest), for assessing lung fluid accumulation, and a communication circuit 328 for interfacing with external components.

The communication circuit 328 can be configured for wirelessly communicating with a communication circuit of the nearby external user-interface device 216. In certain examples, the communication circuit 328 is configured for wirelessly or otherwise communicating with a communication circuit of a distant external user-interface device 218, such as by using a nearby external communication repeater 330. In one such example, the external communication repeater 330 is coupled to the distant external user-interface device 218 via an Internet or telephone connection 332. The Internet or telephone connection 332, in certain examples, allows the external communication repeater 330 to communicate with electronic medical data storage 334. The external user-interface devices 216, 218 can include, among other things, a user-detectable indication 222, for textually or graphically or otherwise relaying information about the one or more responsive acoustic energy echoes 228 or an indication of lung edema fluid status computed therefrom, such as by an internal 302 or external 340 processor circuit. In addition, the external user-interface devices 216, 218 can include a user input device 224 for receiving and storing programming information from a user and communicating such programming information to the CFMD 304 or transducer-bearing leads 306 for implementation. Further yet, the external user-interface devices 216, 218 can include a prompt generating circuit 343 to ready a subject 208 (FIG. 2) for acoustic lung fluid monitoring, such as instructing the subject to lie down and breath smoothly.

In a further example, the communication circuit 328 of the CFMD 304 is communicatively coupled to a communication circuit of another implantable component, such as a blood pressure sensor 336, a heart sound detector circuit 338, or a drug pump 344, as further discussed below.

The present fluid monitoring system 200 monitors and processes information about one or more acoustic energy echoes 228 from a lung 204, 206 in response to one or more acoustic energy beams 226 directed thereto. Thus, the system 200, and more specifically in this example, the CFMD 304, includes a transducer pulse control circuit 352 that is electrically coupled to the acoustic transducer probes 214A, 214B. The transducer pulse control circuit 352 sends electrical current to the one or more acoustic transducer probes 214A, 214B, which are selected by the transducer configuration switch circuit 355 to emit acoustic energy. Returning acoustic electrical energy echoes result in electrical pulses received from the acoustic transducer probes 214A, 214B. Such electrical pulses are sensed by a transducer sense circuit 356 and sent to the internal processor circuit 302, for example, for processing. Functionally, the acoustic transducer probes 214A, 214B receive the electrical current from the transducer control circuit 352 and transform it into sound waves that travel outward. Conversely, when sound or pressure waves hit the acoustic transducer probes 214A, 214B, they emit electrical currents back to the transducer sense circuit 356. In alternative or in addition to the acoustic transducer probes 214A, 214B coupled to the subcutaneous lead 306, the CFMD 304 can include an acoustic transducer 214 therewithin and communicable with the lungs 204, 206 via an acoustic window 354. The acoustic window 354 can be disposed on at least one of a housing (can) or header (FIG. 6B) of the CFMD 304.

The transducer pulse control circuit 352 can be configured to allow a user to set or change, such as by way of the external user-interfaces 216, 218, the frequency, amplitude, or duration of the acoustic energy emitted, or the scan mode of the acoustic transducer probes 214A, 214B. In an example, the acoustic energy emitted to a lung 204, 206 includes one or more ultrasound frequencies such as within an inclusive range of about 20 kHz to about 10 MHz. The frequency, amplitude, or duration of the emitted acoustic energy can also automatically be controlled, such as in response to the detected acoustic energy echoes, for example. Optionally, more than one acoustic energy parameter (e.g., frequency) can be controllably provided by the transducer pulse control circuit 352. This can enhance the sensitivity (e.g., the ability of a detection scheme to effectively detect that which a user desires to detect or treat) or specificity (e.g., the ability of a detection scheme to avoid erroneous or "false" detections that a user desires to detect or treat) of the detection scheme and resulting lung edema fluid status indication. For example, acoustic energy echoes from lung tissue can have different signatures at different injection acoustic energy frequencies. Thus, if the acoustic energy echo information, for example, received at different injection acoustic energy frequencies exhibits similar changes over time, a more confident judgment can be made that the changes are due to fluid accumulation and not to one or more other factors, such as intrinsic properties of lung tissue.

In addition to using information about the one or more acoustic energy echoes 228 from a lung 204, 206 to compute and provide the indication of lung edema fluid status, the present system 200 can also use an indication of one or a combination of thoracic impedance, pulmonary artery blood pressure, at least one heart sound, blood flow, heart size, minute ventilation, venous pressure, or respiration rate to compute and provide such indication. Thus, the system 200 includes an electrical impedance measurement circuit 358, a blood pressure sensor 336, a cardiac sensor circuit 370, a heart sound detector circuit 338, and a respiration sensor circuit 372, for example.

The electrical impedance measurement circuit 358 includes an injected electrical energy generator circuit 360, a voltage measurement circuit 362, an analog-to-digital (A/D) converter (not shown), and a signal processor (not shown and which can be implemented elsewhere, such as with the processor circuit 302) to provide a thoracic impedance-indicating signal to the internal processor circuit 302. The electrical energy generator circuit 360 is configured to generate and inject a current or other electrical energy between at least two electrodes, such as excitation electrodes (e.g., the left ventricular proximal electrode 320 and the can electrode 364). The voltage measurement circuit 362 is configured to measure a potential difference created by the injected energy between the same or different at least two electrodes, such as pick-up electrodes (e.g., the left ventricular distal electrode 322 and the header electrode 366). The voltage measurement circuit 362 can optionally include a demodulator. In various examples, the electrodes used to inject the energy or to measure the resulting potential difference are selected by an electrode configuration switch circuit 368. The A/D converter is used to translate the analog information gathered by the electrical energy generator circuit 360 and the voltage measurement circuit 362 to a proportional digital number. Once so digitized, these values can be applied as inputs to the signal processor for calculating a thoracic impedance value by dividing the potential difference by the injected current (as specified by Ohm's law). A decrease in thoracic impedance over time may correlate to an indication of present or impending fluid accumulation in the lungs 204, 206 and information about such a decrease can be used by the present system 200 to further specify an indication of lung edema fluid status.

The heart sound detection circuit 338 is configured to provide a heart sound indicative signal to the processor circuit 302, such as a signal indicative of one or more of the heart sounds referred to in the art as $S_1$, $S_2$, $S_3$, and $S_4$, and particularly the heart sound referred to in the art as $S_3$, which is representative of left ventricular filling pressure. Without being bound by theory, it is believed that an increase in left ventricular filling pressure causes a pathophysiological cascade, resulting in one or more of a left atrial pressure increase, a pulmonary wedge pressure increase, pulmonary congestion, or pulmonary edema. In an example, the heart sound indicative signal is measured by an implantable accelerometer, microphone or other implantable sensor, such as by using the systems and methods described in Lincoln et al., U.S. Pat. No. 6,665,564, entitled "CARDIAC RHYTHM MANAGEMENT SYSTEM SELECTING A-V DELAY BASED ON INTERVAL BETWEEN ATRIAL DEPOLARIZATION AND MITRAL VALVE CLOSURE," or the systems and methods described in Lincoln et. al., U.S. Pat. No. 6,963,777, entitled "CARDIAC RHYTHM MANAGEMENT SYSTEM AND METHOD USING TIME BETWEEN MITRAL VALVE CLOSURE AND AORTIC EJECTION," each of which is assigned to Cardiac Pacemakers, Inc., and the disclosures of which are incorporated herein by reference in their entirety, including their descriptions of heart sound detection. In another example, the heart sound indicative signal is measured by a caregiver while the subject is lying on his/her left side, and a numerical value indicative of the heart sound frequency or amplitude is user-input into the external user-interface 216, 218. An increase in certain heart sounds, such as the $S_3$ heart sound, frequency or amplitude can correlate to an indication of present or impending fluid accumulation in the lungs 204, 206 and information about such an increase in heart sound frequency or amplitude can be used by the present system 200 to further specify an indication of lung edema fluid status.

Other sensors, such as the blood pressure sensor 336 and a cardiac sensor circuit 370 can be configured to respectively provide a blood pressure-indicative signal indicative of blood pressure in a pulmonary artery and a heart size or blood flow indication to the processor circuit 302. In an example, the blood flow indication can be found using, at least in part, Doppler acoustic energy echo techniques including measuring frequency changes in acoustic energy echoes. An increase in pulmonary artery blood pressure or heart size or a decrease in blood flow can correlate to an indication of present or impending fluid accumulation in the lungs 204, 206 and information about such changes can be used by the present system 200 to further specify an indication of lung edema fluid status.

Further, the respiration sensor circuit 372 can be configured to provide a respiration rate-indicative signal indicative of the subject's respiration rate. In an example, the respiration sensor circuit 372 includes a minute ventilation (MV) sensor. A decrease in respiration rate can correlate to an indication of present or impending fluid accumulation in the lungs 204, 206 and information about such changes can be used by the present system 200 to further specify an indication of lung edema fluid status.

In the interest of stability, repeatability, or sensitivity in measurements, the one or more acoustic energy echoes or other measurements (e.g., thoracic impedance, pulmonary artery blood pressure, at least one heart sound, blood flow, heart size, minute ventilation, venous pressure, or respiration rate) used to compute the indication of lung edema fluid status can be taken at one or both of a desired portion of the respiratory cycle (e.g., end-expiration) or when the subject 208 (FIG. 2) is in a desired physical activity state (e.g., a non-active state), for example. The respiration sensor circuit 372 or the cardiac sensor circuit 370 having the ability to extract respiration information from a cardiac signal can be used by the system 200 to recognize a period of end-expiration. The measurements can also be taken at a specified time period each day, or at a specified posture. For instance, a timing circuit 378 can be used to program measurement to be made at specified time periods, such as at night; while a posture sensor circuit 374 or a physical activity sensor circuit 376 can be used to determine when the subject is in a particular posture or is in a non-active state. The posture sensor circuit 374 can include, among other things, at least one of a tilt switch, a single axis accelerometer, or a multi-axis accelerometer. Programming measurements to be made at specified time periods, such as at night, is another option for the present fluid monitoring systems 200. In such an example, a timing circuit 378 can be used.

An implantable 302 or external 340 processor circuit can include one or more inputs 380 to receive and store in a memory circuit information about the one or more responsive acoustic echoes, the thoracic impedance, the pulmonary artery blood pressure, the at least one heart sound, the blood flow, the heart size, the minute ventilation, the venous pressure, the respiration rate or any other information gathered or received by a circuit or sensor of the system 200. In the example shown, the internal processor circuit 302 includes a responsive echo profiler circuit 382 configured to create an echo profile using signal intensities of the one or more responsive acoustic energy echoes measured by the system 200. In some examples, the created echo profile is communicated to an external user-interface 216, 218 and displayed thereon, with the presentation of a special pattern, such as one or more comet-tail-like artifacts, indicating present or impending lung fluid accumulation. In other examples, the responsive echo profiler circuit 382 includes a learning circuit, which can be trained by a user such that over time, the system 200 can automatically detect an echo profile indicative of present or impending lung fluid accumulation, and more specifically, pulmonary edema.

In various examples, the processor circuit 302, 340 further includes a comparator circuit 384 configured to receive and compare an inputted intensity profile of the acoustic energy echo to a stored specified threshold, template, pattern, or data array, each of which can be based on a subject in a non-edemic state. If it is found that the input data exhibits a characteristic of present or impending lung fluid accumulation, such as an indication that the time between acoustic energy emission and return acoustic echo is decreasing, thoracic impedance is decreasing, heart sound frequency or amplitude is increasing, pulmonary artery blood pressure or heart size is increasing, or blood flow or respiration rate is decreasing, for example, the resulting comparison can be forwarded to a fluid accumulation determination circuit 348, which is configured to use such information to provide a lung edema fluid status indication, such as an indication of present or impending lung edema fluid accumulation.

In various examples, the system 200 can include a regimen control circuit 350 configured for initiating or adjusting a regimen to a subject 208 (FIG. 2) at least in part by using information about one or more responsive acoustic energy echoes from a lung or a computed lung edema fluid status indication. In an example, such regimen includes electrical stimulation, such as cardiac pacing, resynchronization, cardioversion, or defibrillation stimulation, generated by a regimen pulse generator circuit 346 and delivered via one or more electrodes selected by the electrode configuration switch circuit 368. The one or more electrodes are selected individually or in combination to serve as an anode or a cathode in any unipolar, bipolar or multipolar configuration.

In another example, such regimen is provided elsewhere (e.g., communicated to the nearby external user-interface 216 or delivered via an implantable drug pump 344) and includes, for example, a drug dose, a diet regimen, or a fluid intake regimen. In an example, the drug dose can include a set of one or more drug regimen instructions communicated and displayed on the nearby external user-interface 216, and more specifically the user-detectable indication 222. In certain examples, the set of drug regimen instructions includes a suggested daily intake schedule of one or more drugs, such as angiotensin-converting enzyme (ACE) inhibitors, beta blockers, digitalis, diuretics, vasodilators, or the like. The drug dose can be automatically delivered per the suggested daily intake schedule via the implantable drug pump 344 or another drug dispensing device provided within the CFMD 304 or implanted nearby and coupled thereto.

In a similar manner, the diet regimen and the fluid intake regimen can be communicated to the subject 208 (FIG. 2) via the user-detectable indication 222 of the nearby external user-interface 216. In an example, the diet regimen can include a set of one or more dietary instructions to be followed by the subject 208, such as restriction of sodium to 2 grams or less per day and restriction to no more than one alcoholic drink per day. In another example, the fluid intake regimen can include a set of one or more fluid intake instructions to be followed by the subject 208, such as to avoid consuming an excess amount of fluid. FIGS. 3A-3B illustrates just one example of various circuits, devices, and interfaces of the system 200, which are implemented either in hardware or as one or more sequences of steps carried out on a microprocessor or other controller. Such circuits, devices, and interfaces are illustrated separately for conceptual clarity; however, it is to be understood that the various circuits, devices, and interfaces of FIGS. 3A-3B need not be separately embodied, but can be combined or otherwise implemented.

Figure 4:
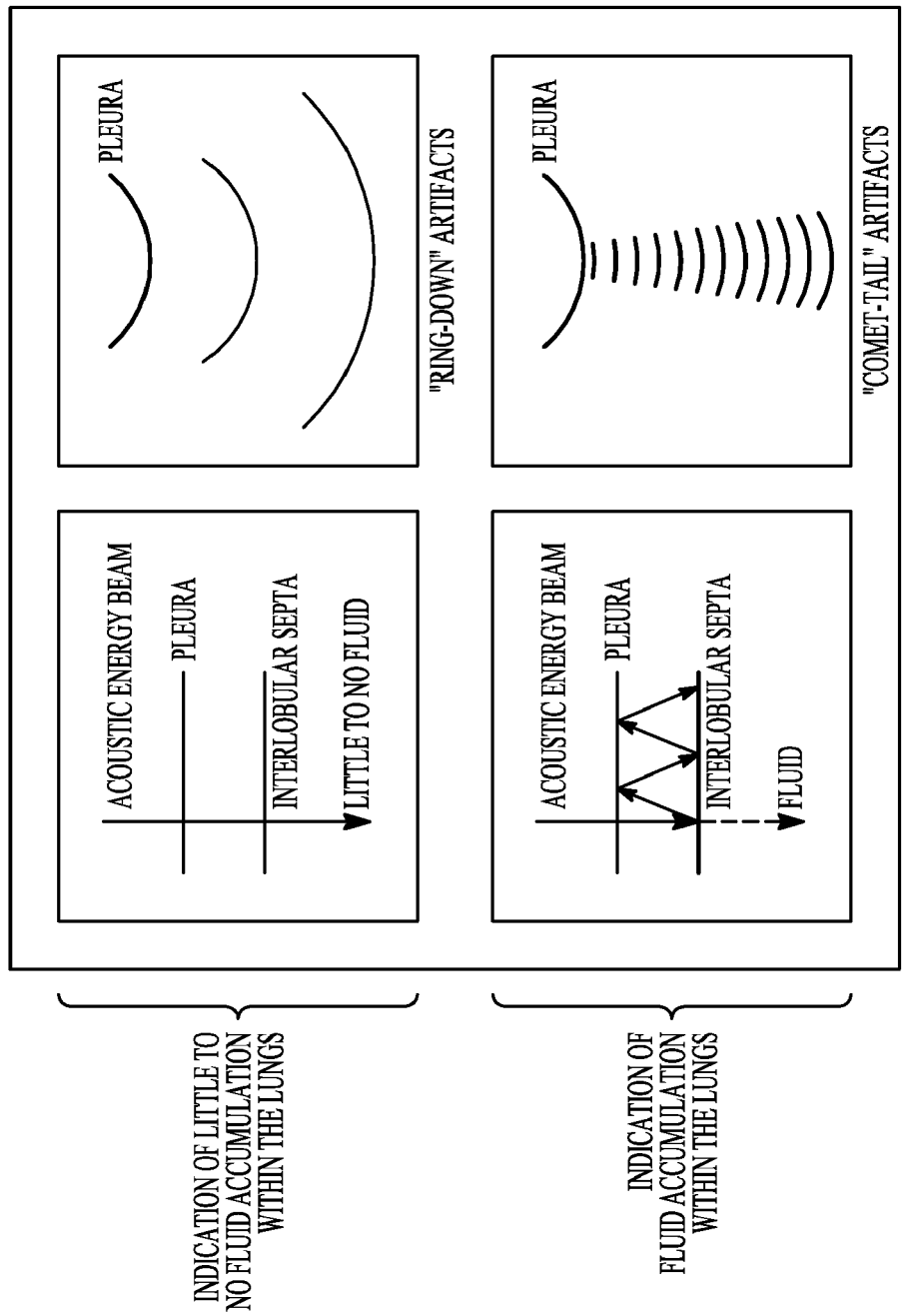
FIG. 4 is a graphical display illustrating one conceptual example of a user-detectable indication of lung edema fluid status found using information about one or more responsive acoustic energy echoes.

FIG. 4 is graphical display, such as may be provided on an external user-interface 216, 218, illustrating one conceptual example of a user-detectable indication of lung edema fluid status found using information about one or more acoustic energy echoes from a lung in response to emitted acoustic energy directed thereto. As discussed above, an acoustic energy beam can be emitted toward a lung 204, 206 (FIG. 2) from an implantable device 212 (FIG. 2) via at least one acoustic transducer probe 214A, 214B (FIG. 3A). As the acoustic energy beam travels toward the lung 204, 206, the energy hits a boundary between tissues and some of the emitted energy gets reflected back to the transducer probe 214A, 214B, which is then relayed to the internal processor circuit 302 (FIG. 3), for example. As shown in FIG. 4, when little to no fluid is present within the interlobular septa, more of the emitted acoustic energy is allowed to travel though the pleura and interlobular septa of the lung 204, 206 until it reaches another boundary at which acoustic reflection may occur. When reflected acoustic energy is displayed, such travel by the reflected acoustic energy can resemble a ring-down artifact as shown. Conversely, when fluid is present within the interlobular septa, more of the emitted acoustic energy is reflected back toward the transducer probe before being allowed to pass through the interlobular septa. When this condition is displayed, such travel by the reflected acoustic energy can resemble a comet-tail-like artifact as shown.

There are a variety of underlying conditions that may lead to thoracic fluid build-up such as pulmonary edema, and a variety of regimen approaches targeting such conditions. The selection of the regimen approach, and the parameters of the particular regimen approach selected, can be a function of the underlying condition and a severity of such condition. For this reason, the present system 200 (FIG. 2) can include a regimen control circuit 350 to appropriately select a regimen given a subject's detected health status.

Figure 5:
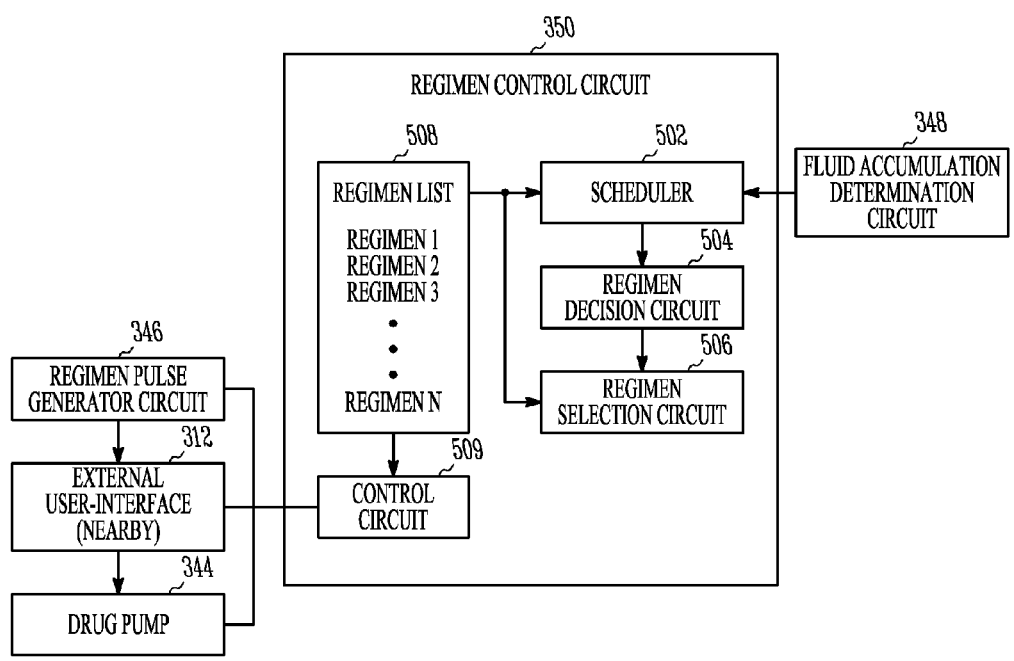
FIG. 5 is a block diagram illustrating one conceptual example of a regiment control circuit that can be used in the present system, the system being configured for monitoring excess fluid accumulation in the thoracic region of a subject using information about one or more responsive acoustic energy echoes from a lung.

FIG. 5 is a block diagram illustrating one conceptual example of a regimen control circuit 350. It can be used to trigger one or more regimens (e.g., therapies) to a subject 208 (FIG. 2), such as in response to information about one or more responsive acoustic energy echoes 228 (FIG. 2) from a lung 204, 206 (FIG. 2), or more specifically, an indication of present or impending lung fluid accumulation (e.g., a lung edema fluid status indication) computed from such information and output by a fluid accumulation determination circuit 348. The regimen control circuit 350 can include an input that receives the indication of present or impending lung fluid accumulation output from the fluid accumulation determination circuit 348. In an example, a scheduler 502 schedules the indications of present or impending lung fluid accumulation. A regimen decision circuit 504 decides whether some form of regimen is warranted. If a regimen is deemed to be warranted, a regimen selection circuit 506 selects one or more appropriate regimens. A control circuit 509 adjusts the selected regimen via an output to one or more of a regimen pulse generator circuit 346, a nearby external user-interface 216, or a drug pump 344, for example.

The regimen control circuit 350 can include a regimen list 508, which can relate the regimens of such list 508 to the highest contributor(s) to the indication of present or impending lung fluid accumulation. In an example, the regimen list 508 includes various possible disease state preventive regimens or secondarily related regimens that the present system 200 can deliver or communicate to the subject 208. The regimen list 508 can be programmed into a CFMD 304 (FIG. 3A) either in hardware, firmware, or software and stored in a memory 342 (FIG. 3A). In another example, the regimen list 508 includes immediate, short-term, intermediate-term, or long-term fluid accumulation preventive therapies. Immediate fluid accumulation preventive therapies can include, by way of example, initiating or changing a drug dose administered to the subject via an implantable drug pump 344 or electrical stimulation administered to the subject 208 via the regimen pulse generator circuit 346. Short-term fluid accumulation preventive regimens can include, by way of example, administering a continuous positive air pressure ("CPAP") dose to the subject 208 or notifying a caregiver to initiate or change the subject's drug dose treatment program. Intermediate-term fluid accumulation preventive regimens can include, by way of example, adjusting the subject's 208 lifestyle such as his or her diet or fluid intake regimen. Finally, long-term fluid accumulation preventive regimens can include, by way of example, notifying the subject 208 or caregiver to alter the drug which takes longer to affect the subject (e.g., beta blockers, ACE inhibitors) or administering CRT to the subject 208.

Each member of the regimen list 508 can be associated with a corresponding time of action, which can include information about one or more of a time for the regimen to become effective or a time after which the regimen is no longer effective. In an example, only one member of the regimen list 508 is invoked at any particular time. In another example, combinations of different regimens are provided at substantially the same time. The various subcircuits in the regimen control circuit 350 are illustrated as such for illustrative purposes only; however, these subcircuits can alternatively be incorporated in the fluid accumulation determination circuit 348 or elsewhere, such as being implemented as a set of programmed instructions performed by a general purpose controller or other circuit.

FIGS. 6A-6D illustrate a heart 202 and lungs 204, 206 of a subject 208 (via a cut-away portion 210) and example implant sites for portions of a system 200 configured for monitoring excess fluid accumulation in the lungs using information about one or more responsive acoustic energy echoes therefrom. As shown in FIGS. 6A-6D, the system 200 can include, at least in part, an implantable device, such as a CFMD 304 or a transducer-bearing lead 306, having at least one acoustic transducer 214 (FIG. 2) configured to emit acoustic energy 226 to a lung 204, 206 and to receive a responsive acoustic energy echo 228 therefrom. In addition, the system 200 can include an electrode-bearing lead 318 having electrodes 320, 322 to sense or stimulate the heart 202, or to provide one or more measurements (e.g., thoracic impedance) that can be combined with the information about the one or more acoustic energy echoes to compute a lung edema fluid status indication.

Figure 6A:
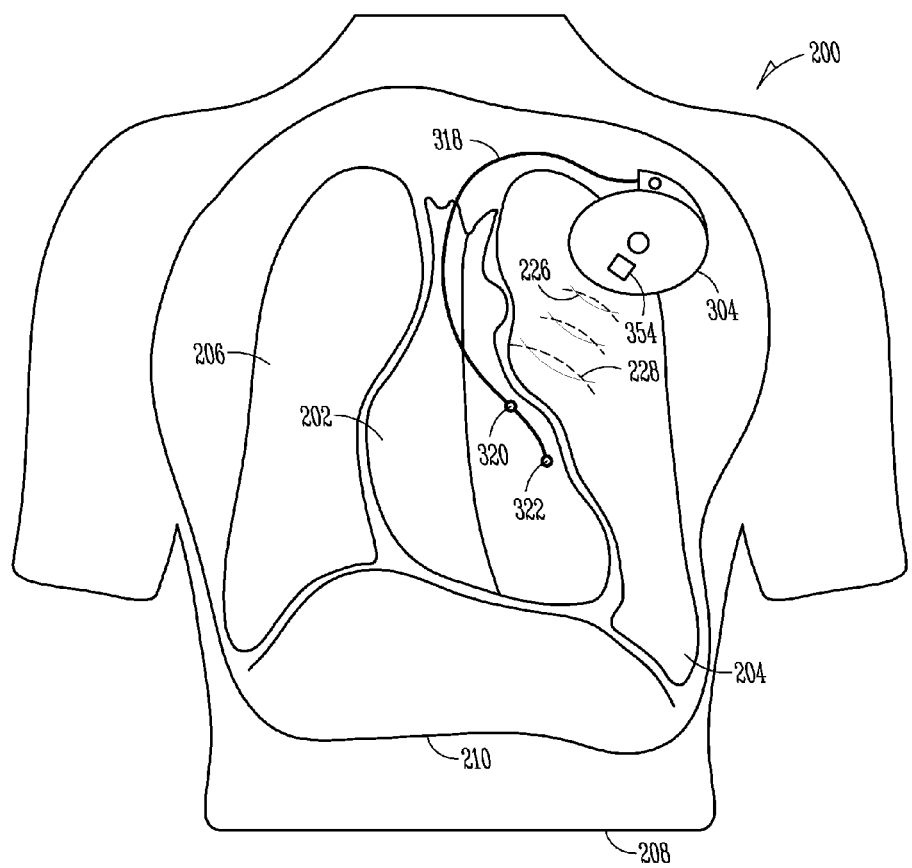
FIGS. 6A-6D are schematic views illustrating various example implant sites and forms of the one or more acoustic transducers used in the present system for emitting acoustic energy to a lung and receiving responsive acoustic energy echoes therefrom.

As shown in the example of FIG. 6A, an acoustic transducer probe can be built on or near the surface of a CFMD 304 housing and oriented such that emitted acoustic energy and responsive echo travel through an acoustic window 354 integrated in the device housing. In an example, the acoustic window 354 is integrated in a lower portion of the device housing nearest the lungs 204, 206. To provide a full or nearly full sweep of the lung(s) 204, 206, an orientation of the acoustic transducer probe can be adjusted via mechanical or electronic mechanisms. In an example, the orientation of the acoustic transducer probe is adjusted electronically using instructions entered by a user into an external user-interface 216, 218. In an example, the orientation of the acoustic transducer probe is adjusted mechanically using set-screw(s) or an implanted, telemetry-controlled motor for optimal signal orientation. In this way, the orientation of the acoustic transducer probe can be changed as desired by a user after implantation, or can be set-up to automatically lock into an algorithm-based optimum orientation. To guide or facilitate orientation selection of the transducer, a material, reference marker, or other device configured to reflect back to the CFMD 304 a unique signal indicative of a then-current transducer relative position (e.g., a signal indicative of a transducer's position relative to the lung boundaries) may be used. The reference marker(s) can be separately implanted and fixated in the subject, such as under the subject's skin.

Alternatively, an array of acoustic transducer probes can be fixedly arranged, such as in a semicircular arrangement, and sequentially addressed via programmed instructions to obtain the sweep of the lung 204, 206. Among other places, the CFMD 304 can be implanted in the left or right pectoral area of the subject 208.

Figure 6B:
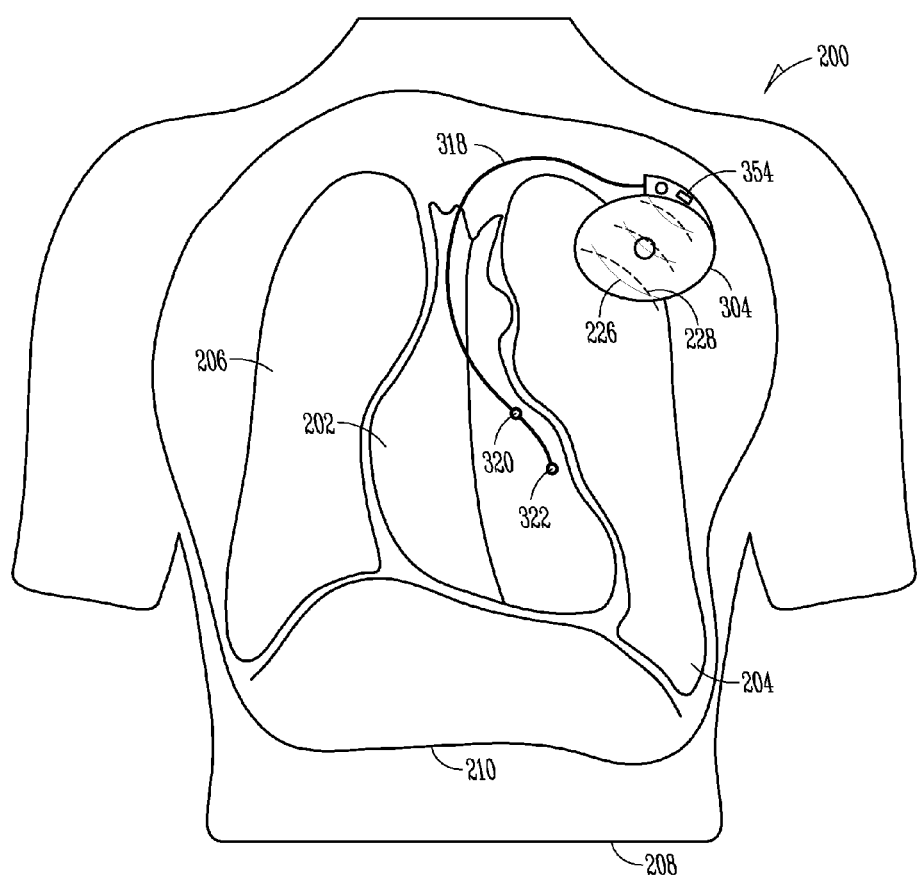

As shown in the example of FIG. 6B, an acoustic transducer probe can be built on or near the surface of a CFMD 304 header and oriented such that emitted acoustic energy and responsive echo travel through an acoustic window 354 integrated in the device housing. In an example, the CFMD 304 acoustic transducer probe, whether built on the housing or header, is oriented, at least in part, using a suture or cyanoacrylate adhesive.

Figure 6C:
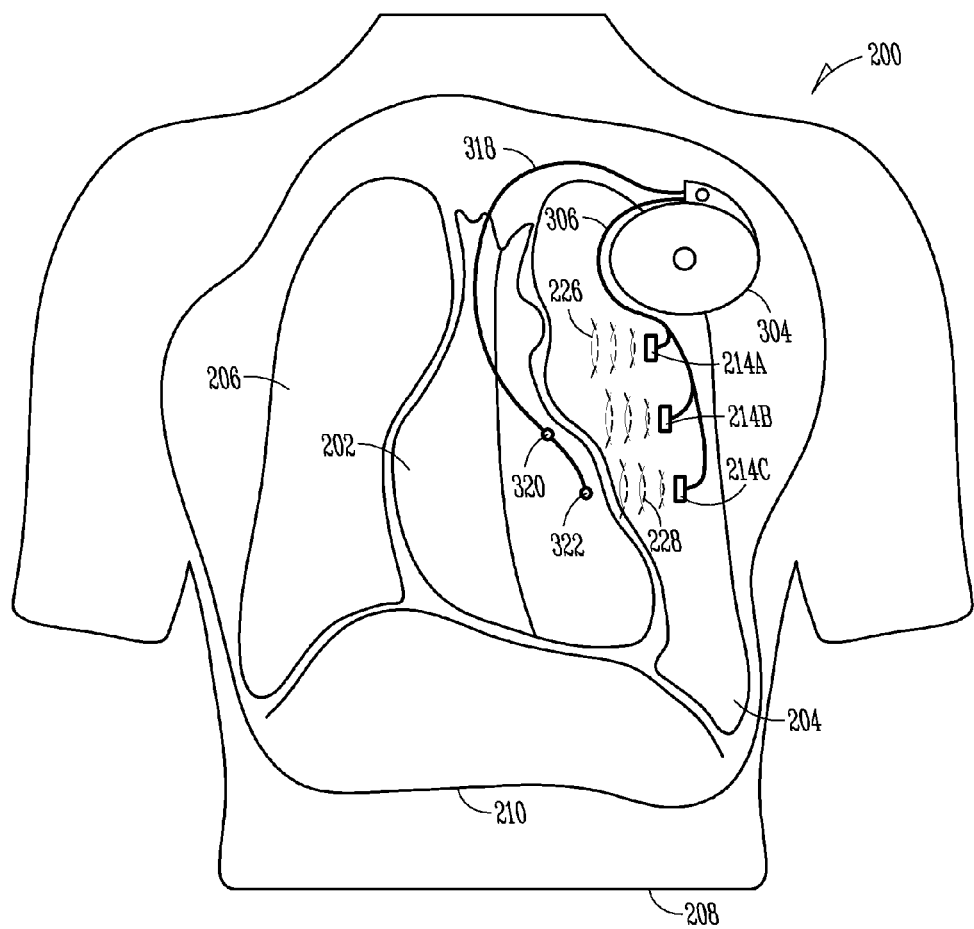

As shown in the example of FIG. 6C, one or more acoustic transducer probes 214A, 214B, 214C can be coupled with a subcutaneous lead 306, the latter of which is connected to a CFMD 304, in a substantially linear or segmented array. In the case of an array, each acoustic transducer probe can have its own amplifier, control, timing electronics, or logic such that the associated acoustic energy beam 226 might be focused or diffused depending on the desired function or effect, or steered to a desired location, or that the beam can be swept to cover several sites in sequential order, or any combination thereof. In an example, one or more acoustic transducer probes can be used to emit acoustic energy, while one or more other acoustic transducer probes are used to receive echoes resulting therefrom. It is believed that at higher emitted energy frequencies, the emitting and receiving transducer probes should be better aligned than at lower emitted energy frequencies. In this example, a plurality of acoustic transducer probes 214A, 214B, 214C are arranged in a generally vertical manner to allow for concurrent fluid monitoring of a lung 204, 206. A variation of this system 200 can be implemented with multiple leads 306 with at least one acoustic transducer probe 214. Although not shown, a pressure sensor, such as a pulmonary artery pressure sensor, can be coupled to the electrode-bearing lead 318 or the transducer-bearing lead 306.

Figure 6D:
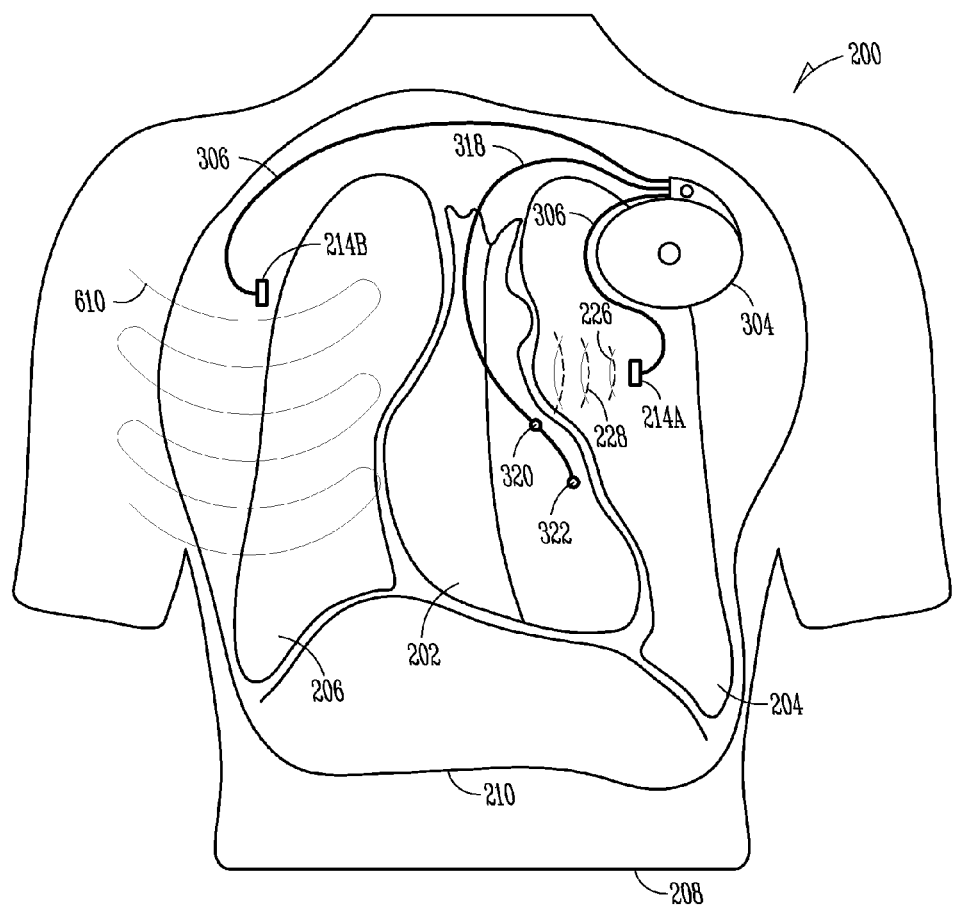

The transducer-bearing lead 306 can be implanted on any location in the pectoral region, including both left and right pectoral areas, as shown in FIG. 6D, to provide concurrent fluid monitoring of both the left 204 and right 206 lungs. Optionally, the one or more acoustic transducer probes 214A, 214B are positioned between the ribs 610 and the lungs 204, 206. This example illustrates that acoustic transducer probes for monitoring lung fluid may be positioned near or far from a CFMD 304 to which it is coupled, such as via one or more transducer-bearing leads 306, or wirelessly, such as by using a wireless ultrasonic communication signal between the transducer and the CFMD 304. Advantageously, this allows for the possible placement of acoustic transducer probes in non-conventional CFMD 304 places. An acoustic transducer probe's location or orientation can optionally be fixed using, for example, one or more or any combination of sutures, helical coils, barbs, tines, clips, or the like, or by bonding onto an outer surface thereof materials which are known to stimulate cellular growth or adhesion (e.g., cyanoacrylate adhesive). Conversely, a drug eluting substance or a biocompatible coating can be disposed along the transducer-bearing lead body 306 to prevent fibrotic or other cellular growth thereto.

Figure 7:
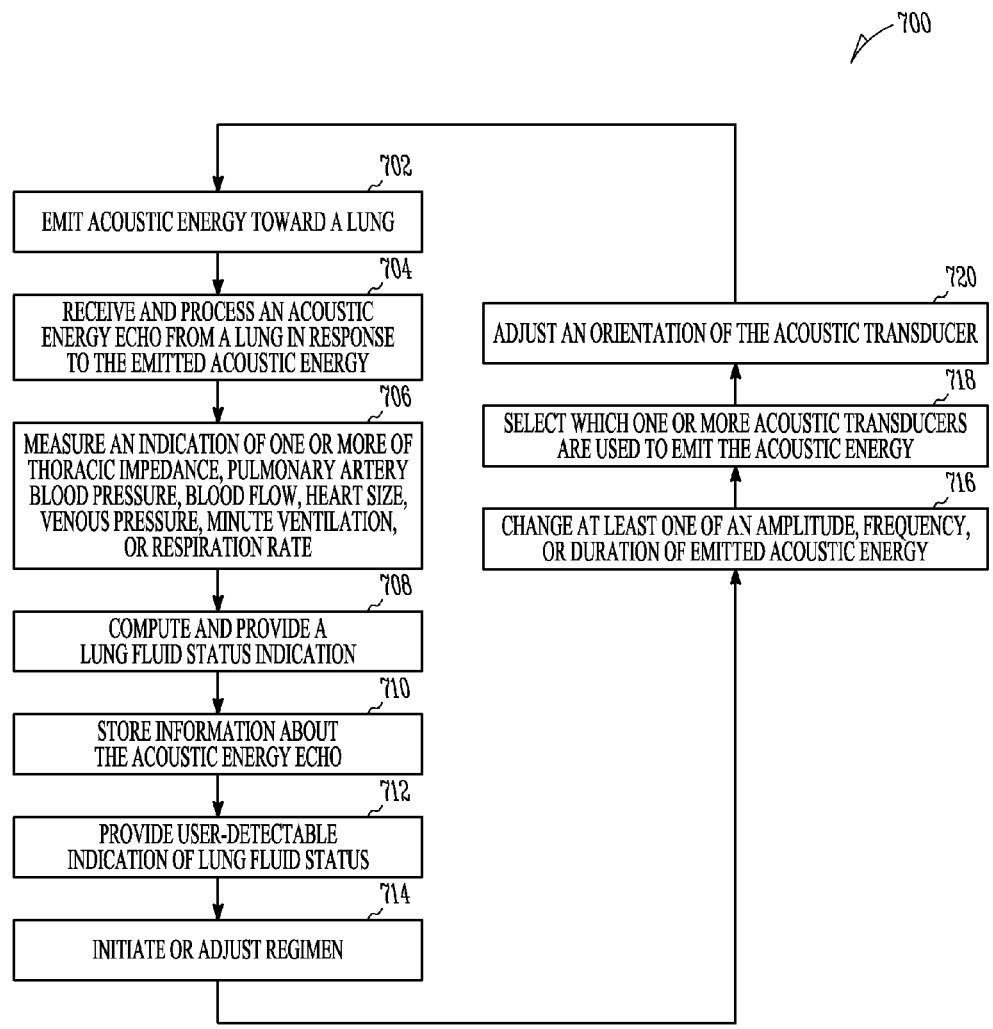
FIG. 7 is a block diagram illustrating one conceptual method of monitoring excess fluid accumulation in the thoracic region of a subject by computing and providing a lung edema fluid status indication, the indication found using information about one or more responsive acoustic energy echoes from a lung.

FIG. 7 is a block diagram 700 illustrating one conceptual method of monitoring excess fluid accumulation in the thoracic region of a subject, and more specifically, one or both of the subject's lungs using information about responsive acoustic energy echoes. At 702, an acoustic energy beam is emitted toward a lung using a fully implantable device, such as a CFMD or a transducer-bearing lead, having at least one acoustic transducer. In an example, emitting the acoustic energy includes emitting ultrasonic energy toward the lung. In another example, emitting the acoustic energy includes steering the acoustic energy beam from at least one of a left or a right pectoral region of the subject. In yet another example, emitting the acoustic energy includes steering the acoustic energy from a lateral region between a subject's ribs and left or right lung.

At 704, one or more acoustic energy echoes are received and processed. In an example, the acoustic energy echoes are received at the same acoustic transducer that was used to emit the acoustic energy beam at 702. In another example, the acoustic energy echoes are received at a different acoustic transducer than was used to emit the acoustic energy beam at 702. In one such example, the acoustic transducer used to receive the acoustic energy echoes is positioned laterally opposite the acoustic transducer used to emit the acoustic energy beam. In such an example, acoustic transmission characteristics such as transit time, amplitude, and frequency can be used to determine a lung fluid edema status.

At 706, an indication of one or more of thoracic impedance, pulmonary artery blood pressure, blood flow, heart size, venous pressure, respiration rate, or minute ventilation is measured. At 708, a lung edema fluid status indication is computed and provided. In some examples, the lung edema fluid status indication is computed solely from information about the one or more acoustic energy echoes, such as information that the number of acoustic energy echoes received has increased or the time between successive acoustic energy echoes has decreased. In other examples, the lung edema fluid status indication is computed using information about one or more of thoracic impedance, pulmonary artery blood pressure, blood flow, heart size, venous pressure, respiration rate, or minute ventilation in addition to the information about the one or more acoustic energy echoes.

At 710, information about the acoustic energy echoes and optionally, information one or more of thoracic impedance, pulmonary artery blood pressure, blood flow, heart size, venous pressure, respiration rate, or minute ventilation is stored. At 712, a user-detectable indication of lung edema fluid status, such as an indication of present or impending pulmonary edema, is provided. In an example, a positive indication of lung edema fluid status is provided at an external user-interface via the display of one or more comet-tail-like artifacts. In some examples, the presence of one or more comet-tail-like artifacts can be visually recognized by a user. In other examples, the presence of one or more comet-tail-like artifacts is automatically recognized by the present fluid monitoring system. At 714, a regimen is initiated or adjusted in response to the positive indication of present or impending lung fluid accumulation.

At 716, 718, and 720, one or more parameters of the emitted acoustic energy beam is optionally changed. At 716, for example, at least one of an amplitude, frequency, or duration of the acoustic energy beam is programmably or automatically changed. At 718, a selection of which one or more acoustic transducers are to be used during a fluid monitoring measurement is performed. Finally, at 720, an orientation of one or more acoustic transducers is programmably or automatically adjusted to obtain a desired acoustic energy echo response to an emitted acoustic energy beam.

Conclusion:

Chronic diseases, such as heart failure, can benefit from close medical management to reduce hospitalizations, morbidity, and mortality. Because such disease status evolves with time, frequent physician follow-up examinations are often necessary. The approach of periodic in-person follow-up is unsatisfactory for diseases like heart failure, in which acute, life-threatening exacerbations (e.g., heart failure decompensation and associated acute pulmonary edema) can develop between physician follow-up examinations. Pulmonary edema is a serious medical condition in which an excess amount of fluid accumulates in or around a subject's lungs. This condition can, and often does, result from heart failure. Pulmonary edema can require immediate care. While it can sometimes prove fatal, the outlook for subjects possessing pulmonary edema can be good upon early detection and prompt treatment.

Advantageously, the present systems and methods can provide for enhanced, yet less complex monitoring of excess fluid accumulation in a subject's thoracic region and thus, can provide a more timely, accurate, or perhaps cheaper detection of pulmonary edema or other thoracic fluid accumulation than is currently available. Such detection can be made possible by, among other things, generating one or more responsive energy echoes from a lung by emitting acoustic energy thereto and using information about such acoustic energy echoes to compute and provide a lung edema fluid status indication.

Closing Notes:

The above Detailed Description includes references to the accompanying drawings, which form a part of the Detailed Description. The drawings show, by way of illustration, specific embodiments in which the invention can be practiced. These embodiments are also referred to herein as "examples." All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "cardiac function management device" or simply "CFMD" is used to include, but is not limited to, implantable cardiac rhythm management (CRM) systems such as pacemakers, cardioverters/defibrillators, pacemakers/defibrillators, biventricular or other multisite resynchronization or coordination devices such as cardiac resynchronization therapy (CRT) device, subject monitoring systems, neural modulation systems, or drug delivery systems. In this document, the terms "acoustic energy" includes any sound, pressure, vibration, or the like at frequencies within or outside the range of hearing, such as ultrasound energy.

In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine-implemented or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code may be tangibly stored on one or more volatile or non-volatile computer-readable media during execution or at other times. These computer-readable media may include, but are not limited to, hard disks, removable magnetic disks, removable optical disks (e.g., compact disks and digital video disks), magnetic cassettes, memory cards or sticks, random access memories (RAM's), read only memories (ROM's), and the like.

The above description is intended to be illustrative, and not restrictive. For example, the above-described examples (or one or more features thereof) may be used in combination with each other. Other embodiments can be used, such as by one of ordinary skill in the art upon reviewing the above description. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. In addition, while the majority of this patent document discusses the monitoring of fluid in a thoracic region of a subject, the present systems and methods can be used in ways similar to those discussed herein to monitor fluid accumulation in other regions of a subject's body. Thus, the following claims are hereby incorporated into the Detailed Description, with each claim standing on its own as a separate embodiment. The scope of the invention should be determined with reference to the appended claims, along with the full scope of equivalents to which such claims are entitled.

The Abstract is provided to comply with 37 C.F.R. §1.72 (b), to allow the reader to quickly ascertain the nature of the technical disclosure. It is submitted with the understanding that it will not be used to interpret or limit the scope or meaning of the claims.

What is claimed is:

1. A system comprising:
   a fully implantable device including an acoustic transducer that emits acoustic energy to a lung and receives a responsive acoustic energy echo from the lung; and
   an implantable or external processor circuit configured to receive information about the acoustic energy echo and configured to detect increases in the number of acoustic energy echoes received per nit of time, the processor circuit including a comparator circuit configured to compare an energy profile of the received acoustic energy echo to a stored specified threshold, algorithm, pattern, or data array,
   wherein the processor circuit is configured to compute and provide a worsening heart failure decomposition indication from the detected increase in echoes per unit of time and information about the energy profile comparison.

2. The system of claim 1, comprising an external user-interface device communicatively coupled to the implantable device and including a user-detectable indication of worsening heart failure decompensation derived from the information about the acoustic energy echo and the information about the energy profile comparison.

3. The system of claim 1, comprising a transducer pulse control circuit configured to control at least one of an amplitude, a frequency, or a duration of the acoustic energy emitted from the acoustic transducer and thereby provide a level of confidence in the computed worsening heart failure decompensation indication.

4. The system of claim 1, comprising a timing circuit configured to trigger a recurrent emitting of the acoustic energy synchronized with a specified phase of one or both of a subject's respiratory cycle or cardiac cycle.

5. The system of claim 1, comprising a regimen control circuit configured to initiate or adjust a regimen provided to a subject using information about the acoustic energy echo and the information about the energy profile comparison.

6. The system of claim 1, comprising a pressure sensor configured to provide a blood pressure-indicating signal indicative of blood pressure in a pulmonary artery; and wherein the processor circuit includes an input to receive the blood pressure-indicating signal, and the processor circuit is configured to also use information about the blood pressure-indicating signal to compute the worsening heart failure decompensation indication.

7. The system of claim 1, comprising an electrical impedance measurement circuit configured to inject an electrical energy between two or more electrodes and to concurrently measure a response thereto in a thoracic region of a subject between the same or different two or more electrodes to provide a thoracic impedance-indicating signal; and wherein the processor circuit includes an input to receive the thoracic impedance-indicating signal, and the processor circuit is configured to also use information about the thoracic impedance-indicating signal to compute the worsening heart failure decompensation indication.

8. The system of claim 1, wherein the implantable device includes a cardiac function management device having a device body, the device body including an acoustic window disposed such that the acoustic energy is emitted or responsive acoustic energy is received therethrough in a direction of a lung when the device body is implanted in a pectoral region.

9. The system of claim 1, wherein the implantable device includes one or more subcutaneous leads, each lead having a lead body extending from a proximal end portion to a distal end portion and having an intermediate portion therebetween; and wherein at least one of the intermediate portion or the distal end portion includes the acoustic transducer.

10. The system of claim 1, wherein the acoustic energy includes a frequency within an inclusive range of about 20 KHz to about 10 MHz.

11. A method comprising:

emitting acoustic energy defined by a first set of acoustic energy parameters toward a lung using a fully implantable device;

receiving and processing one or more acoustic energy echoes;

computing a lung edema fluid status indication from information about the one or more acoustic energy echoes, including determining at least one of an increased number, a decreased number, or a pattern of acoustic energy echoes received, or a decrease in time between successively received acoustic energy echoes; and verifying and displaying an accuracy of the lung edema fluid status indication, including programmably or automatically changing at least one of an amplitude, a frequency, pulse shape, or a duration of the emitted acoustic energy to define a second set of acoustic energy parameters, and comparing acoustic energy echo information related to the first set of acoustic energy parameters with acoustic energy echo information related to the second set of acoustic energy parameters.

12. The method of claim 11, comprising programmably or automatically selecting which one or more acoustic transducers are used to emit the acoustic energy.

13. The method of claim 11, comprising storing information about instances of the one or more acoustic energy echoes over a period of time that exceeds a respiration cycle length.

14. The method of claim 11, comprising measuring an indication of pulmonary artery blood pressure; and using the indication of pulmonary artery blood pressure to compute the lung edema fluid status indication.

15. The method of claim 11, comprising measuring an indication of thoracic impedance; and using the indication of thoracic impedance to compute the lung edema fluid status indication.

16. The method of claim 11, comprising measuring an indication of at least one heart sound; and using the indication of heart sound to compute the lung edema fluid status indication.

17. The method of claim 11, comprising measuring at least one of a blood flow indication, a heart size indication, a venous pressure indication, a respiration rate indication, or an associated rate of change thereof; and using at least one of the blood flow indication, the heart size indication, the venous pressure indication, the respiration rate indication, or the associate rate of change thereof to compute the lung edema fluid status indication.

18. The method of claim 11, comprising adjusting an orientation of an acoustic transducer via adjusting a set-screw associated with the transducer.

19. The method of claim 11, comprising adjusting an orientation of an acoustic transducer via activating an implanted motor associated with the transducer.

20. The method of claim 11, wherein emitting acoustic energy includes emitting ultrasonic energy toward the lung using the fully implantable device.

21. The method of claim 11, wherein emitting acoustic energy toward the lung includes steering the acoustic energy from at least one of a left or a right pectoral region of a subject.

22. The method of claim 11, wherein emitting acoustic energy toward the lung includes using at least one reference marker disposed on a lead or fixated to a portion of a subject.

23. The system of claim 1, wherein the worsening heart failure decompensation indication includes recognition of a signature pattern, the pattern including one or more comet-tail-like artifacts.

24. The system of claim 7, wherein the acoustic energy emitted to the lung to produce the acoustic energy echo information and the electrical energy injected between two or more electrodes to produce the thoracic impedance-indicating signal measurement is synchronized with a period of end-expiration of a respiratory cycle.

25. The method of claim 11, comprising measuring a minute ventilation indication; and using the minute ventilation indication in conjunction with information about the one or more acoustic energy echoes to compute the lung edema fluid status indication.

* * * * *